US00PP35303P2

(12) United States Plant Patent
Blake

(10) Patent No.: US PP35,303 P2
(45) Date of Patent: Aug. 8, 2023

(54) ***CROCOSMIA* HYBRID PLANT NAMED 'DARK FIRE'**

(50) Latin Name: ***Crocosmia* hybrid**
Varietal Denomination: DARK FIRE

(71) Applicant: Jaime Blake, Bressingham (GB)

(72) Inventor: Jaime Blake, Bressingham (GB)

( * ) Notice: Subject to any disclaimer, the term of this patent is extended or adjusted under 35 U.S.C. 154(b) by 0 days.

(21) Appl. No.: 18/088,060

(22) Filed: Dec. 23, 2022

(51) Int. Cl.
*A01H 5/02* (2018.01)
*A01H 6/00* (2018.01)

(52) U.S. Cl.
USPC ..... Plt./419
CPC ..... *A01H 6/00* (2018.05)

(58) Field of Classification Search
USPC ..... Plt./419
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Crocosmia* hybrid plant named 'DARK FIRE' is disclosed, characterized by unique flower coloration, having red petals edged with bright yellow. Plants are non-rampant. Foliage coloration is distinctively bronze-purple in full sun. The new variety is a dwarf plant, typically used for outdoor garden or container use.

2 Drawing Sheets

Latin name of the genus and species: *Crocosmia* hybrid.
Variety denomination: 'DARK FIRE'.

BACKGROUND OF THE INVENTION

The new cultivar is a product of chance discovery. The new variety was discovered as a chance seedling emerging among a planting of various *Crocosmia* hybrid plants. The inventor discovered this seedling during 2005 in a commercial nursery in Bressingham, United Kingdom.

Asexual reproduction of the new cultivar 'DARK FIRE' was first performed during 2013 at a commercial nursery in Bressingham, United Kingdom. This was conducted by division. Subsequent asexual propagation and confidential testing over several years has shown that the unique features of this cultivar are stable and have been reproduced true to type for five successive generations.

SUMMARY OF THE INVENTION

The cultivar 'DARK FIRE' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'DARK FIRE' grown in Dayton, Oreg. These characteristics in combination distinguish 'DARK FIRE' as a new and distinct *Crocosmia* hybrid cultivar:

1. Bronze-purple leaves in full sun.
2. Distinct flower color; red petals edged with bright yellow.
3. Non-rampant growth.
4. Dark leaves appear olive green and brown on the same plant as sunlight hits them.

PARENT COMPARISON

The parentage cannot be accurately identified.

COMMERCIAL COMPARISON

Plants of the new cultivar 'DARK FIRE' are similar to plants of *Crocosmia* 'Gerbe D'Or', unpatented, in most horticultural characteristics, however, plants of the new cultivar 'DARK FIRE' differ in the following;

1. 'Gerbe D'Or' has yellow flowers which are slightly pendent, 'Dark Fire' has bi-colored flowers which are held flatter, closer to vertical.
2. 'Gerbe D'Or' has brown leaves without the olive coloration of 'Dark Fire'
3. 'Gerbe D'Or' is about 30 cm taller Plants of the new cultivar 'DARK FIRE' are similar to plants of the unpatented commercial variety, *Crocosmia* 'Saracen' in most horticultural characteristics, however, plants of the new cultivar 'DARK FIRE' differ in the following;

1. 'Saracen' has larger flowers which are not bi-colored as are the flowers of 'Dark Fire'.
2. 'Saracen' is shorter than 'Dark Fire', by about 20 to 30 cm.
3. 'Saracen' has brown leaves which are wider than those of 'Dark Fire'.
4. 'Saracen' is later flowering than 'Dark Fire'.

BRIEF DESCRIPTION OF THE PHOTOGRAPHS

Figure 1:
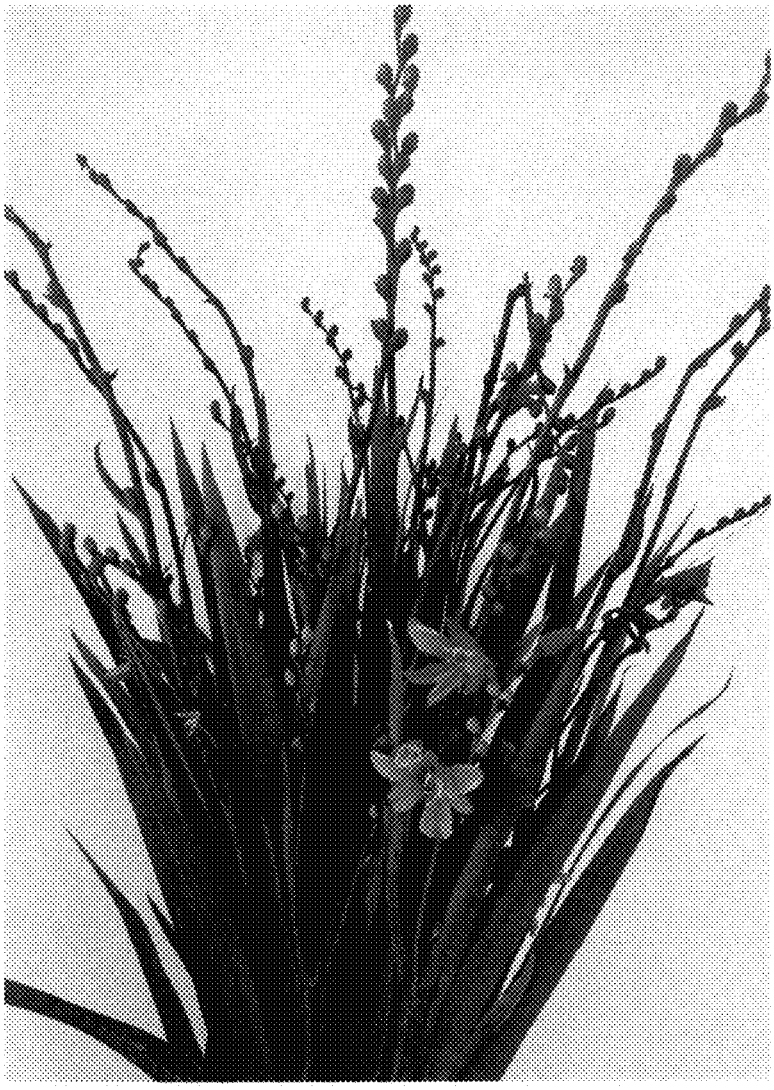

The accompanying photograph in FIG. 1 illustrates in full color a typical flowering plant of 'Dark Fire'.

Figure 2:
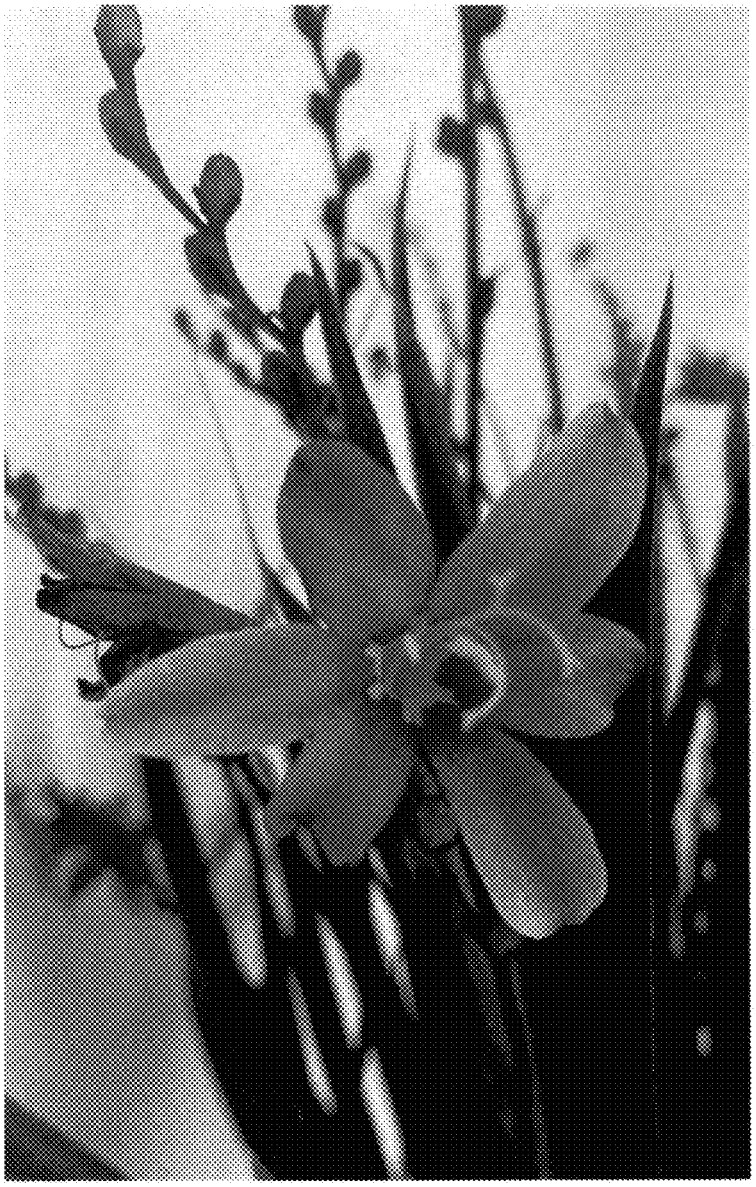

FIG. 2 illustrates in full color a close up view of a typical flower of 'DARK FIRE'.

Age of the plant is approximately 18 months, grown outdoors in Dayton, Oreg. in a 2-gallon pot. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'DARK FIRE' plants grown outdoors and in a nursery in Dayton, Oreg. Plants are approximately 18 months old, in a 2-gallon nursery container. Temperatures ranged from −8° C. to 20° C. at night to 5° C. to 35° C. during the day. Measurements and numerical values represent averages of typical plant types.

Botanical classification: *Crocosmia* hybrid 'DARK FIRE'.

PROPAGATION

Typical method: Division.

PLANT

Growth habit: Upright, non-branching perennial forming basal clumps.

Pot size of described plant: 5 gallon.

Height: Approximately 45 cm to top of highest leaf. Approximately 55 to 60 cm to top of highest inflorescence.

Plant spread: Approximately 30 cm.

Growth rate: Moderate.

FOLIAGE

Leaf:

- *Arrangement.*—Alternate.
- *Average length.*—Approximately 35 to 40 cm.
- *Average width.*—Approximately 1.7 cm.
- *Shape of blade.*—Ensiform.
- *Apex.*—Acute.
- *Base.*—Sheathed. Sheath about 2 cm long and 1.6 mm wide.
- *Margin.*—Entire.
- *Attitude.*—Erect.
- *Texture of top surface.*—Ribbed, very prominent mid-vein.
- *Texture of bottom surface.*—Ribbed, very prominent mid-vein.
- *Quantity of leaves per plant.*—Approximately 80.
- *Color.*—Young foliage upper side: Near RHS Yellow-Green 147A heavily flushed Greyed-Red 183A. Margin Greyed-Yellow 162a flushed Yellow 13C. Young foliage under side: Near RHS Yellow-Green 147A heavily flushed Greyed-Red 183A. Mature foliage upper side: Near RHS Yellow-Green 147A heavily flushed Greyed-Red 183A. Mature foliage under side: Near RHS Yellow-Green 147A heavily flushed Greyed-Red 183A.
- *Venation.*—Type: Parallel. Venation color upper side: Mid-Vein near RHS Green 139A, other veins indistinguishable from leaf blade. Venation color under side: Mid-Vein near RHS Green 139A, other veins indistinguishable from leaf blade.

FLOWER

Natural flowering season: Summer.

Inflorescence type: Scorpioid cyme.

Rate of flower opening: About 2 weeks from moderately tight bud to open flower.

Flower longevity on plant: Individual flower approximately 10 days, depending on environmental conditions.

Quantity of flowers: 10 to 12 flowers and buds per inflorescence.

Inflorescence size:

- *Height.*—Approximately 15 cm.
- *Width.*—Approximately 3 cm.

Corolla:

- *Shape.*—Short funnel with 6 long lobes.
- *Size.*—Length: Approximately 4.0 cm. Width: Approximately 4.5 cm at widest point. Lobe Length: Approximately 2.5 cm. Lobe Width: 1.2 cm. Tube Length: 1.1 cm. Tube Diameter: 7 mm at opening.
- *Lobe margin.*—Entire.
- *Lobe shape.*—Elliptic.
- *Lobe apex.*—Rounded.
- *Lobe texture.*—Glabrous all surfaces.

Color:

Lobes: When opening:

- *Outer surface.*—Near RHS Red 42A. Thick streak near Yellow-Orange 17B along margin.
- *Inner surface.*—Near RHS Red 42A, lightly speckled Orange-Red N30A and N30B. Thick streak near Yellow-Orange 17B along margin.

Fully opened:

- *Outer surface.*—Near RHS Red 42A. Thick streak near Yellow-Orange 17B along margin.
- *Inner surface.*—Lower ½ near Red 43A. Upper ½ near Yellow-Orange 23B heavily streaked Red 43A. Thick streak near Orange Yellow-Orange 17B along margin.

Throat: When opening:

- *Outer surface.*—Near RHS Red 42A.
- *Inner surface.*—Near RHS Yellow-Orange 23A.

Fully opened:

- *Outer surface.*—Near RHS Red 43A.
- *Inner surface.*—Near RHS Yellow-Orange 23A.

Bud:

- *Shape.*—Narrow ovate.
- *Length.*—Approximately 1 cm.
- *Diameter.*—Approximately 7 mm.
- *Color.*—Near RHS Orange-Red N34A, base near Yellow-Orange 14B.

Sepals: Not Present.

Spathe valve: Typically 1, awn-like, 8 mm to 15 mm long, about 3 mm wide. Colored near RHS Yellow-Green 147A heavily flushed Greyed-Red 183A.

Pedicels: Not present, flowers sessile.

Flowering stem:

- *Length.*—Approximately 10 to 15 cm, arising about mid leaf.
- *Width.*—Approximately 3 to 5 mm.
- *Strength.*—Very strong.
- *Color.*—Near RHS Yellow-Green 147A heavily flushed Greyed-Red 183A.
- *Texture.*—Glabrous.

Fragrance: None.

REPRODUCTIVE ORGANS

Stamens:

- *Number.*—Average 3.
- *Filament length.*—Approximately 1.5 cm.
- *Filament color.*—Near RHS Yellow-Orange 16A.
- *Anther length.*—7 mm.
- *Anther color.*—Near RHS Yellow-Orange 15B.
- *Anther shape.*—Linear.

*Pollen.*—Scant to none.

*Protrusion.*—Very slightly protruding past lobes.

Pistil:

*Number.*—1.

*Length.*—Approximately 3.3 cm.

*Style color.*—Near RHS Yellow-Orange 17C.

*Stigma.*—Shape: 3-parted into elongated linear sections. Color: Near RHS Yellow-Orange 16A.

*Ovary color.*—Near RHS Yellow-Green 147D flushed 146D.

OTHER CHARACTERISTICS

Disease/pest resistance: Neither resistance nor susceptibility to normal diseases and pests of *Crocosmia* has been observed.

Seeds and fruits: Not observed.

Temperature tolerance: USDA Zones 4 through 9.

What is claimed is:

1. A new and distinct cultivar of *Crocosmia* hybrid plant named 'DARK FIRE' as herein illustrated and described.

* * * * *